United States Patent
Vilks

(10) Patent No.: US 9,220,834 B2
(45) Date of Patent: Dec. 29, 2015

(54) PRESSURE SENSING IN MEDICAL INJECTION SYSTEMS

(71) Applicant: ACIST Medical Systems, Inc., Eden Prairie, MN (US)

(72) Inventor: Clinton Scott Vilks, Plymouth, MN (US)

(73) Assignee: ACIST Medical Systems, Inc., Eden Prairie, MN (US)

(*) Notice: Subject to any disclaimer, the term of this patent is extended or adjusted under 35 U.S.C. 154(b) by 400 days.

(21) Appl. No.: 13/721,485

(22) Filed: Dec. 20, 2012

(65) Prior Publication Data

US 2014/0180084 A1 Jun. 26, 2014

(51) Int. Cl.
| | |
|---|---|
| *A61M 37/00* | (2006.01) |
| *A61M 1/00* | (2006.01) |
| *A61M 5/00* | (2006.01) |
| *A61M 25/00* | (2006.01) |
| *A61M 1/36* | (2006.01) |
| *A61M 5/168* | (2006.01) |

(52) U.S. Cl.
CPC ........... *A61M 5/007* (2013.01); *A61M 25/0009* (2013.01); *A61M 1/3639* (2013.01); *A61M 5/16854* (2013.01); *A61M 2205/3331* (2013.01); *Y10T 29/49764* (2015.01); *Y10T 29/49826* (2015.01)

(58) Field of Classification Search
CPC .................. A61M 1/3639; A61M 2205/3331; A61M 5/16854
See application file for complete search history.

(56) References Cited

U.S. PATENT DOCUMENTS

| | | | |
|---|---|---|---|
| 5,024,099 A | 6/1991 | Lee | |
| 5,031,460 A | 7/1991 | Kanenobu et al. | |
| 5,105,820 A | 4/1992 | Moriuchi et al. | |
| 5,808,203 A | 9/1998 | Nolan et al. | |
| 7,722,557 B2* | 5/2010 | Sano et al. | 604/6.09 |

(Continued)

FOREIGN PATENT DOCUMENTS

| | | |
|---|---|---|
| EP | 1213035 A1 | 6/2002 |
| EP | 1655044 A2 | 5/2006 |

(Continued)

OTHER PUBLICATIONS

International Search Report and Written Opinion for International Application No. PCT/US2013/075774, mailed May 16, 2014, 13 pages.

Force Sensors Line Guide; Jun. 2009, 3 pages, Honeywell International Inc., Golden Valley, Minnesota.

*Primary Examiner* — Rebecca E Eisenberg
(74) *Attorney, Agent, or Firm* — Fredrikson & Byron, P.A.

(57) ABSTRACT

A pressure sensor for a medical injection system includes a cuff, a transducer embedded in the cuff, and a force transmitting member coupled to the transducer and exposed at an inner surface of the cuff, such that an outer surface of a tubing line of a fluid circuit of the system, when fitted within the cuff, contacts the force transmitting member. A limited length of the tubing line may have a greater compliance than a remainder of the line, in which case, the pressure sensor cuff fits around and encloses the limited length to provide support against plastic deformation, when pressures within the line are significantly greater than atmospheric. The pressure sensor may detect whether or not the cuff is properly fitted around the tubing line, and/or determine a characteristic of the tubing line.

12 Claims, 4 Drawing Sheets

(56) References Cited

U.S. PATENT DOCUMENTS 7,905,246 B2 3/2011 Wilson et al.
2011/0009800 A1* 1/2011 Dam et al. .................. 604/6.16

FOREIGN PATENT DOCUMENTS

| WO | 9854555 A1 | 12/1998 |
|---|---|---|
| WO | 2004061399 A2 | 7/2004 |

* cited by examiner

US 9,220,834 B2

PRESSURE SENSING IN MEDICAL INJECTION SYSTEMS

TECHNICAL FIELD

The present disclosure pertains to medical injection systems and more particularly to pressure sensing therein.

BACKGROUND

FIG. 1 is a perspective view of an exemplary medical injection system 100 (the ACIST $CV_i$® system) for delivering a contrast agent into a patient's vascular system for medical imaging. FIG. 1 illustrates a first fluid reservoir 132 for supplying a syringe-type positive displacement pump of an injector/pressurizing unit 130, via a fill tubing line 27-F, and an injection tubing line coupled to unit 130 for injection of, for example, a radiopaque contrast agent, into a patient's vascular system via an inserted catheter (not shown), for example, coupled to a patient tubing line 122 at a connector assembly 120 thereof. FIG. 1 further illustrates a second fluid reservoir 138 from which a diluent, such as saline, is drawn by a peristaltic pump 106 through yet another tubing line 128 that feeds into tubing line 122. A manifold valve 124 and associated sensor 114 control the flow of fluids into tubing line 122, from pressurizing unit 130 and from tubing line 128.

A pressure sensor assembly is shown integrated into line 128 to monitor the patient's blood pressure, in between injections of contrast agent. During an injection of contrast agent from pressurizing unit 130, the aforementioned manifold valve 124 is switched to allow the relatively high pressure flow through line 122 and into the patient's vascular system, and to isolate line 128 and pressure sensor assembly from the flow; then, after the injection, valve 124 is switched to put pressure sensor assembly in fluid communication with patient tubing line 122 to monitor the patient's vascular/hemodynamic pressure. Pressure sensor assembly may be the LogiCal® system available from Smiths Medical International, or the Meritrans®, available from Merit Medical Systems, Inc., both of which are intended for use in a single medical procedure. Alternative means for pressure monitoring in medical injection systems, like system 100, for example, being more robust and/or configured for more flexible integration therein, are desired.

SUMMARY

A pressure sensor for a medical injection system, according to some embodiments of the present invention, includes a cuff, a transducer embedded in the cuff, between inner and outer surfaces thereof, and a force transmitting member coupled to the transducer and exposed at the inner surface of the cuff, such that an outer surface of a tubing line, when properly fitted within the cuff, contacts the force transmitting member. According to some embodiments, a fluid circuit assembly includes the pressure sensor and a specialized tubing line, wherein the specialized tubing line has a limited length of greater compliance than a remainder of the tubing line; the pressure sensor cuff is configured to fit around and enclose the limited length of the tubing line, such that the inner surface of the cuff supports the enclosed second length of the tubing against plastic deformation, when fluid filling the lumen of the tubing line is at pressures significantly greater than atmospheric pressure, for example, during injections.

According to some embodiments and methods a microprocessor of the pressure sensor is programmed to characterize a transducer signal in response to the force transmitting member, after the cuff is fitted around the tubing line, and while the lumen of the tubing line is open to atmospheric pressure, to detect whether or not the cuff is properly fitted around the tubing line, and/or to determine a characteristic of the tubing line, wherein the characteristic may indicate whether or not the tubing line is suitable for proper function of the pressure sensor cuff therewith. Fitting the cuff around the tubing line may be accomplished by either axially or radially inserting the tubing line into the cuff, the latter being accommodated by a slit formed in the cuff, according to some embodiments. The microprocessor of the sensor may be adapted to send a signal to an injector of the injection system, after detecting the proper tubing line and fit thereof in the cuff, wherein the signal unlocks the injector for operation.

BRIEF DESCRIPTION OF THE DRAWINGS

The following drawings are illustrative of particular methods and embodiments of the present disclosure and, therefore, do not limit the scope of the invention. The drawings are not to scale (unless so stated) and are intended for use in conjunction with the explanations in the following detailed description. Methods and embodiments will hereinafter be described in conjunction with the appended drawings, wherein like numerals denote like elements, and.

DETAILED DESCRIPTION

The following detailed description is exemplary in nature and is not intended to limit the scope, applicability, or configuration of the invention in any way. Rather, the following description provides practical illustrations for implementing exemplary methods and embodiments. Examples of constructions, materials and dimensions are provided for selected elements, and all other elements employ that which is known to those of skill in the field of the invention. Those skilled in the art will recognize that many of the examples provided have suitable alternatives that can be utilized.

Figure 1:
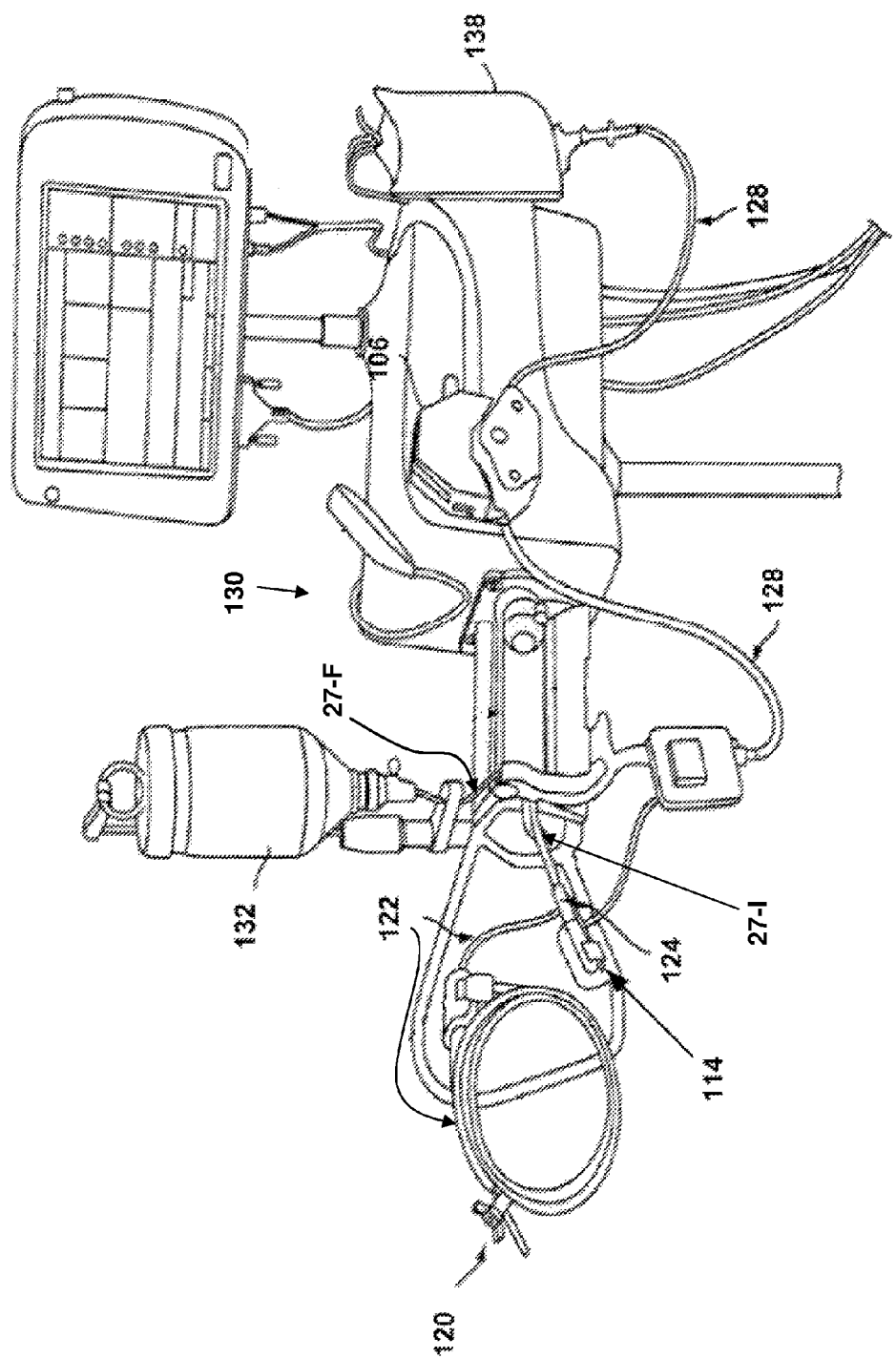
FIG. 1 is a perspective view of an exemplary medical injection system.
Figure 2A:
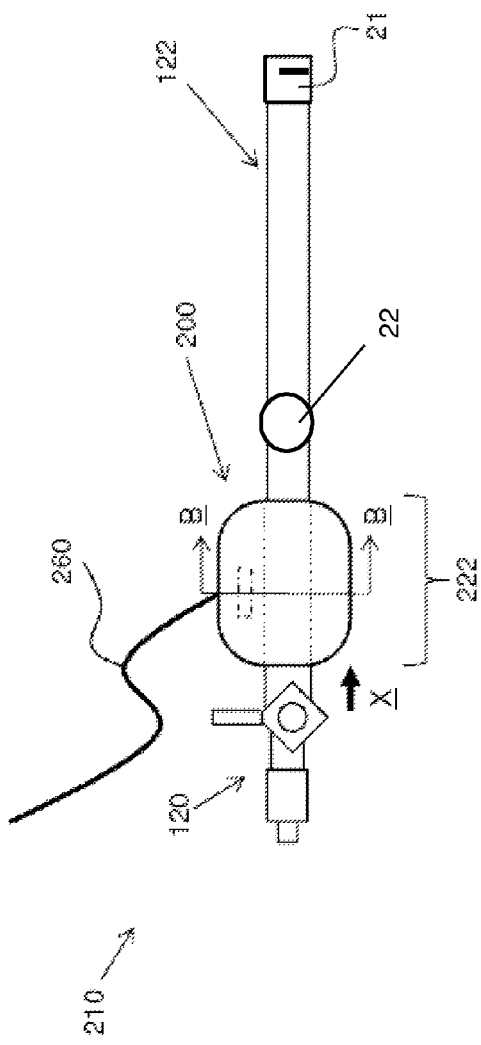
FIG. 2A is a plan view of a fluid circuit assembly for a medical injection system, according to some embodiments.

FIG. 2A is a plan view of a fluid circuit assembly 210 for a medical injection system, for example, system 100 of FIG. 1. FIG. 2A illustrates assembly 210 including a pressure sensor 200, which is fitted around patient tubing line 122, in proximity to connector assembly 120. FIG. 2A further illustrates tubing line 122 including a proximal connector 21 (i.e. a Luer fitting), for example, to connect assembly 210 to the above-described manifold valve 124 of system 100. According to some embodiments, pressure sensor 200 is employed to measure system pressures, for example, generated by injector 130 (FIG. 1), and tubing line 122 has a wall thickness and stiffness to withstand relatively high injection pressures (i.e. up to approximately 1200 psi), wherein line 122 may be formed from nylon-reinforced polyurethane, and has a nominal outer diameter of approximately 0.188 inch (4.78 mm) and a nominal wall thickness of approximately 0.05 inch (1.27 mm). According to some alternate embodiments, pressure sensor 200 may be employed to measure both system pressures and physiologic pressures (i.e. blood pressure) of a patient, or just physiologic pressures, in which case, tubing line 122 may include a check valve 22 integrated therein. According to some preferred alternate embodiments, wherein pressure sensor 200 measures physiologic pressures, tubing line 122 is replaced with a specialized tubing line, for example, line 322 of FIG. 3A, which will be described in greater detail below.

Figure 2B:
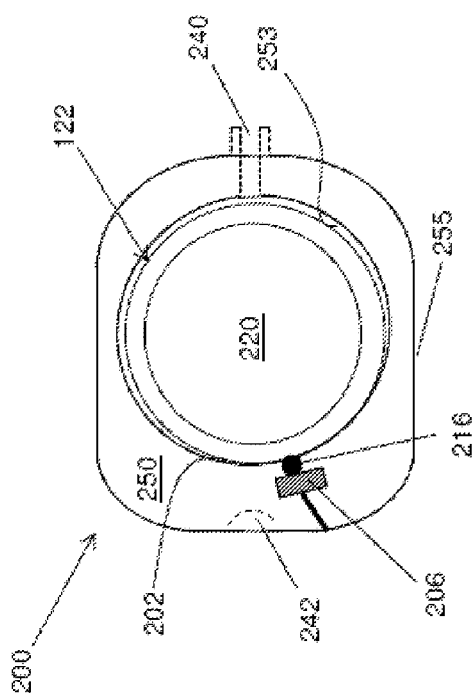
FIG. 2B is a cross-section view of a pressure sensor of the assembly, taken through section line B-B of FIG. 2A, according to some embodiments.

FIG. 2B is a cross-section view of assembly 210, taken through section line B-B of FIG. 2A. FIG. 2B illustrates pressure sensor 200 including a cuff 250, a force transmitting member 216, and a transducer 206 coupled to force transmitting member 216, wherein transducer 206 is embedded between an inner surface 253 and an outer surface 255 of cuff 250. FIG. 2B further illustrates force transmitting member 216 exposed at inner surface 253 of cuff 250, and inner surface 253 configured to fit around a length tubing line 122, for example, a length 222 shown in FIG. 2A. According to the illustrated embodiment, pressure sensor cuff 250 is sized so that an outer surface 202 of tubing line 122 is in intimate contact with force transmitting member 216, when cuff 250 is properly fitted around tubing line 122; thus, a wall 12 of tubing line 122 transmits, to force transmitting member 216, a pressure of fluid within a lumen 220 of tubing line 122, which is in communication with the patient's vascular system when an inserted catheter (not shown) is connected to tubing line 122 at connector assembly 120. According to an exemplary embodiment, length 222 is between approximately 1 inch and 1.5 inch (2.5-3.8 cm), inner surface 253 of cuff 250 defines a diameter of approximately 0.19 inch (0.48 cm), for the aforementioned 0.188 inch (4.78 mm) outer diameter of line 122, and force transmitting member 216 and transducer 206 are a stainless steel ball/plunger and piezoresistive silicon die, respectively, for example, similar to that employed in the FSS series force sensors of Honeywell (Golden Valley, Minn.).

Force transmitting member 216, in conjunction with transducer 206, generates response signals corresponding to the pressure of fluid in lumen 220, and an electrical lead wire 260 (FIG. 2A) may conduct the signals from transducer 206 to a system microprocessor, which may generate plots of blood pressure vs. time, for example, on a display of a control panel, like panel 152 of system 100 (FIG. 1). Alternately, sensor 200 may include means for wireless transmission of the signals, according to methods known in the art.

Dashed lines in FIG. 2B illustrate an optional slit 240 formed through cuff 250 and a corresponding living hinge 242 formed in an opposing side of cuff 250, which allow for cuff 250 to open for radial insertion of tubing line 122 therein. Alternately, tubing line 122 may be axially inserted into cuff 250, for example, via arrow X of FIG. 2A, so that cuff 250 need not include slit 240 and hinge 242.

Figure 3A:
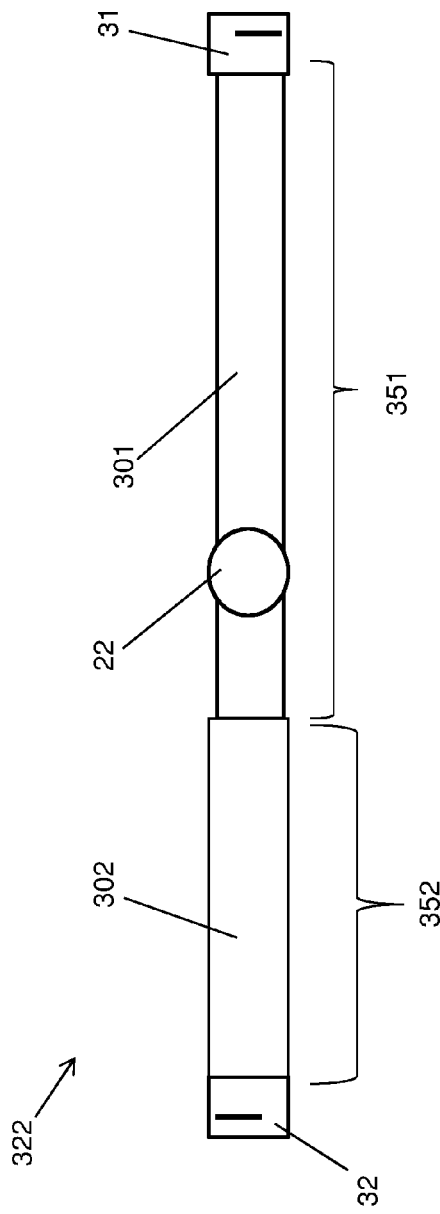
FIG. 3A is a plan view of a specialized tubing line for a fluid circuit assembly, according to some alternate embodiments.
Figure 3B:
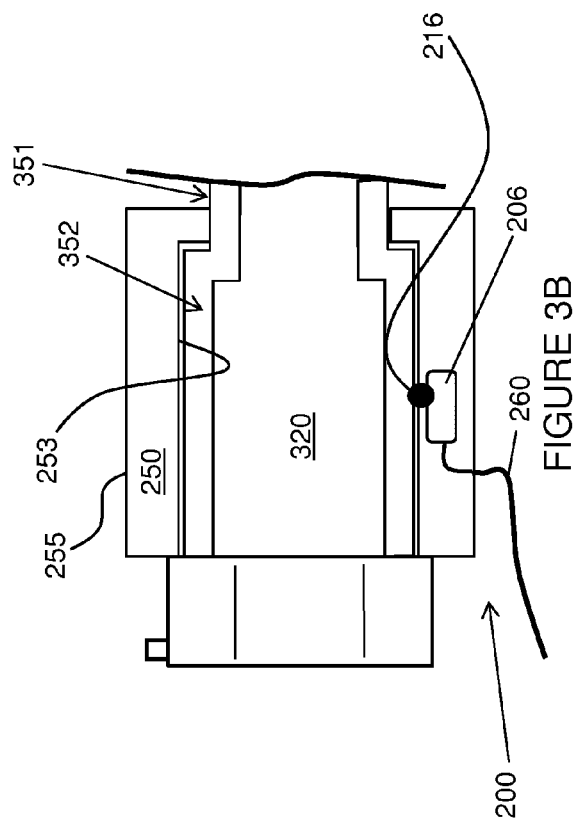
FIG. 3B is an axial cross-section view through a pressure sensor fitted around a length of the tubing line shown in FIG. 3A.

FIG. 3A is a plan view of the aforementioned specialized tubing line 322 for incorporation in a fluid circuit assembly, according to some alternate embodiments, such as assembly 310 of FIG. 3B, which is shown in axial cross-section. FIG. 3A illustrates tubing line 322 including a first length 351, which extends from a proximal connector 31, and a second length 352 which extends between first length 351 and a distal connector 32. Tubing line 322 may be substituted for tubing line 122 in system 100 (FIG. 1), wherein proximal connector 31 is coupled to manifold valve 124, and distal connector is coupled to connector assembly 120. FIG. 3B illustrates pressure sensor 200 fitted around, and enclosing second length 352 of tubing line 322 such that an outer surface 302 of second length 352 contacts force transmitting member 216 of pressure sensor 200. According to the illustrated embodiment, a wall of first length 351 has a compliance, or stiffness which can withstand relatively high injection pressures without plastic deformation, while a wall of second length has a greater compliance, or lower stiffness, which allows second length 352 to provide a more sensitive/responsive interface for transmitting lower, physiologic pressures of fluid within lumen 320 of tubing line 322 to transducer 206, via force transmitting member 216. Thus, with further reference to FIG. 3B, cuff 250 of pressure sensor 200, by enclosing an entirety of second length 352, supports the more compliant wall thereof against plastic deformation during relatively high pressure injections.

With further reference to FIG. 3A, it should be noted that the location of second length 352, in proximity to distal connector 32, allows pressure sensor cuff 250 to be positioned in relatively close proximity to a catheter access point of a patient, when the catheter is connected, via connector assembly 120, at distal connector 32. FIG. 3A further illustrates check valve 22 integrated into first length 351 of tubing line 322, according to preferred embodiments, wherein valve 22 blocks back-flow from distal connector 32 and provides a pressure backstop for improved signal response during physiologic pressure monitoring, when connector assembly 120 couples tubing line 322 to a catheter inserted in a patient's vascular system.

With further reference to FIG. 3B, a thickness of the wall of second length 352 of tubing line 322 may be less than that of first length 351, to increase the compliance of second length 352. According to an exemplary embodiment, tubing line 322 is formed from the aforementioned nylon-reinforced polyurethane, wherein first length 351 has a nominal wall thickness of approximately 0.05 inch (1.27 mm) and second length 352 has a nominal wall thickness no greater than approximately 0.01 inch (0.254 mm). However, according to alternate embodiments, a thickness of tubing line 322 along both lengths 351, 352 may be the same, wherein second length 352 is formed from a more compliant material than first length 351, for example, from polyurethane without the nylon reinforcement and/or polyurethane of a reduced durometer. According the illustrated embodiment, an outer diameter of second length 352 is preferably greater than that of first length 351, for example, as a means for detecting the proper placement of cuff 250 along tubing line 322, as described below.

Figure 4:
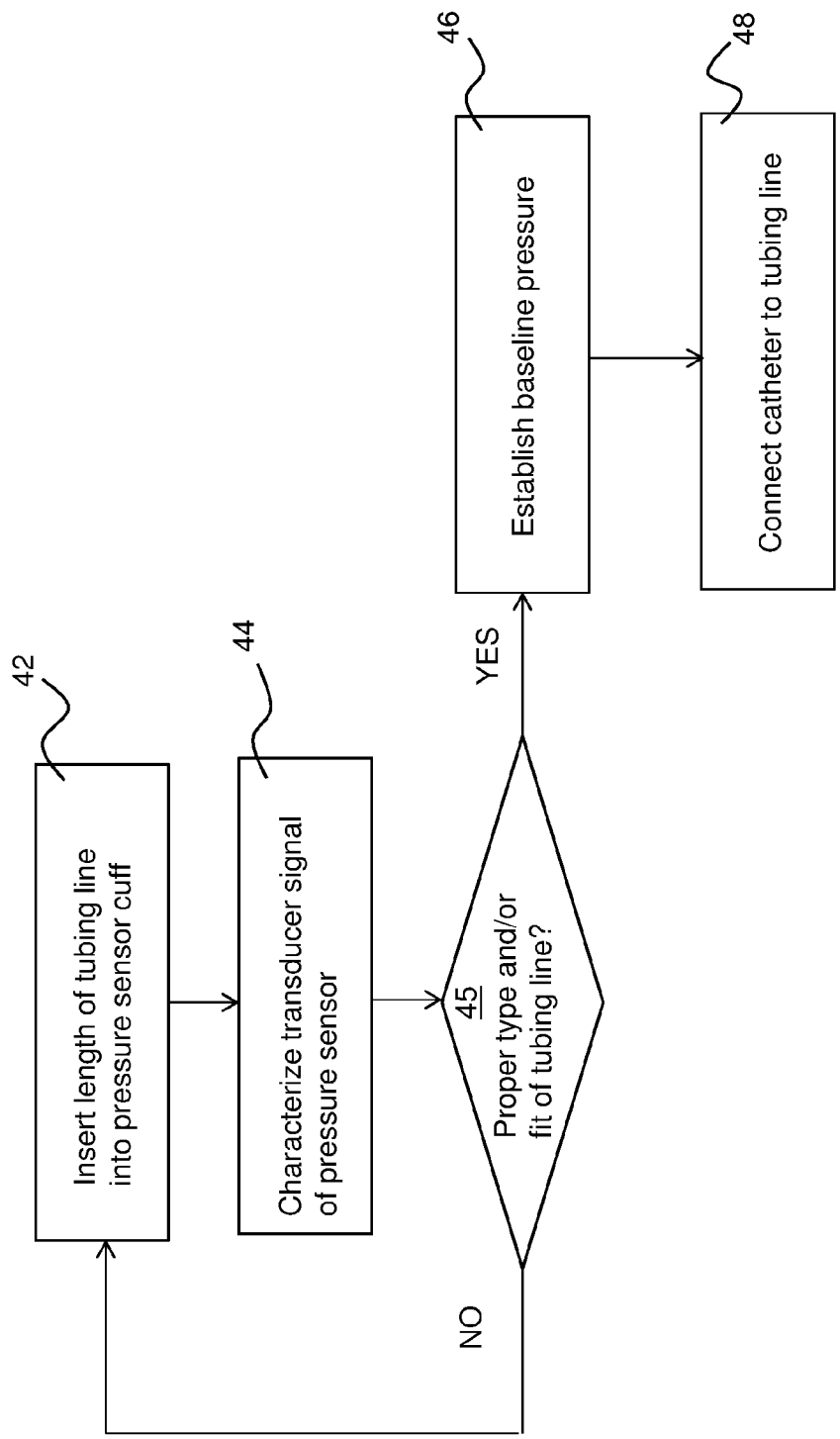
FIG. 4 is a flow chart outlining some methods of the present invention.

FIG. 4 is a flow chart outlining some methods of the present invention for assembling a fluid circuit of a medical injection system, for example, like system 100. In an initial step 42, a pressure sensor cuff, for example, cuff 250 of sensor 200, is positioned around a length of a tubing line, for example, tubing line 122 or 322, by inserting the length into the cuff, for example, either by opening a side slit in a sidewall of the cuff to radially insert the length of tubing line therein, or by axially inserting the length of tubing line into the cuff. If the latter, the length of the tubing line may be compressed to facilitate insertion into the cuff and then expanded within the cuff to assure that a force transmitting member, for example, member 216, of the pressure sensor contacts an outer surface of the inserted length of tubing line.

Once the length of tubing line is inserted into the pressure sensor cuff, and while a lumen of the tubing line is open to atmospheric pressure, a transducer signal, for example, generated by transducer 206 in response to force transmitting member 216, may be characterized by a microprocessor coupled to the transducer, per step 44, for example, in order to detect whether or not the pressure sensor cuff is properly positioned around the length of the tubing line, and/or whether or not the length of tubing line is a type suitable for proper function of the pressure sensor cuff; that is, whether or not the tubing line has a sufficient outer diameter and/or a compliant enough wall for the transmission of pressure therethrough to the contacting force transmitting member of the pressure sensor. The microprocessor, according to some embodiments, is one dedicated to pressure sensor 200, for example, built into cuff 250; alternately the microprocessor may be one in the same as the aforementioned system microprocessor, for example, being coupled to sensor 200 via electrical lead wire 260. In either case, according to some preferred embodiments, the microprocessor is also coupled to an injector of the injection system, for example, injector 130 of system 100 (FIG. 1), in order to send a signal to the injector, after detecting the proper tubing line and fit thereof in the cuff, wherein the signal unlocks the injector for operation. As mentioned above, according to those embodiments that include the above-described specialized tubing line, an outer diameter of a more compliant section of the specialized tubing line, for example, second length 352 of line 322, is preferably larger than a remainder of the tubing line, such that if the pressure sensor cuff is positioned around the stiffer section of the line, for example, first length 351 of line 322, a gap, or clearance between the force transmitting member, at the inner surface of the cuff, and the tubing line prevents transmission of sufficient force from the tubing line to the force transmitting member to prevent detection of a proper fit. According to some embodiments and methods, detection of too great a tubing compliance may protect against inadvertent reuse of a tubing line which is intended for single use. At decision point 45, if the length of tubing line is not properly fitted within the pressure sensor cuff, or is not the proper type of tubing line, no signal is sent to unlock the injector and the tubing line is either re-inserted, per step 42, or the proper type of tubing line is exchanged for the detected improper type, and inserted into the pressure sensor cuff, per step 42.

Once the proper type and fit of tubing line is detected, per decision point 45, and while the fitted tubing line remains open to atmospheric pressure, a baseline pressure, for example, zero with respect to atmospheric, is established for the pressure sensor cuff, per step 46, and a signal may be generated by the microprocessor to unlock the injector for operation, preferably after, step 48, in which a catheter, which is inserted within a patient's vascular system, is connected to the tubing line, for example, via connector system 120 (FIGS. 1, 2A). Thus, the assembled fluid circuit allows for the monitoring of system pressures and/or the patient's blood pressure, via transmission through the wall of the length of tubing line inserted within the pressure sensor cuff.

Preferably, the above described embodiments of pressure sensor 200 are reusable over a number of medical imaging procedures, since none of the components thereof are exposed to bodily fluids. Furthermore, the above described configurations of pressure sensor 200 allow for positioning and repositioning thereof in a fluid circuit of a medical injection system without concern for introducing air bubbles into the fluid circuit. In addition, according to some embodiments, the aforementioned ball/plunger and piezoresistive silicon die, when employed for the force transmitting member and transducer, respectively, form a robust pressure sensor of sufficient range and sensitivity useful for both physiologic and system pressure monitoring (i.e. pressures ranging from approximately 0 psi to approximately 1200 psi). But, according to alternate embodiments, the pressure sensor components have a more limited range and sensitivity tailored to measure relatively high system pressures (i.e. up to 1200 psi), for example, through the wall of a high pressure tubing line (i.e. tubing line 122, as described above).

In the foregoing detailed description, the invention has been described with reference to specific embodiments. However, it may be appreciated that various modifications and changes can be made without departing from the scope of the invention as set forth in the appended claims.

I claim:

1. A fluid circuit assembly for a medical injection system comprising:
   a tubing line defining a lumen extending from a proximal connector of the tubing line to a distal connector of the tubing line; and
   a pressure sensor comprising a cuff, a force transmitting member, and a transducer, the cuff including an inner surface and an outer surface, the inner surface configured to fit around the tubing line, the transducer being embedded in the cuff, between the inner surface and the outer surface, and the force transmitting member being coupled to the transducer and exposed at the inner surface of the cuff; and
   wherein the cuff is sized so that an outer surface of the tubing line contacts the force transmitting member of the pressure sensor, when the cuff is properly fitted around the tubing line; wherein:
   the tubing line includes a first length and a second length, the first length extending distally from the proximal connector and having a wall of a first compliance, and the second length extending distally from the first length and having a wall of a second compliance, the second compliance being greater than the first compliance;
   the inner surface of the pressure sensor cuff is configured to fit around and enclose the second length of the tubing line; and
   when fluid filling the lumen of the tubing line is at pressures significantly greater than atmospheric pressure, and the pressure sensor cuff is properly fitted around the second length of the tubing line, the inner surface of the cuff supports the enclosed second length of the tubing line against plastic deformation,
   wherein the pressure sensor further comprises a microprocessor coupled to the transducer thereof for receipt of transducer signals, the microprocessor being programmed to characterize a transducer signal in response to the force transmitting member, after the cuff is fitted around the tubing line, and while the lumen of the tubing line is open to atmospheric pressure, to detect whether or not the cuff is properly fitted around the tubing line to enclose and support the second length of the tubing line, and
   wherein the microprocessor is adapted to send a signal to an injector of the injection system, after detecting that the cuff is properly fitted around the tubing line, the signal unlocking the injector for operation.

2. The assembly of claim 1, wherein the second length of the tubing line is located in close proximity to the distal connector.

3. The assembly of claim 1, wherein the second length of tubing line has a larger outer diameter than the first length of the tubing.

4. A fluid circuit assembly for a medical injection system comprising:
   a tubing line defining a lumen extending from a proximal connector of the tubing line to a distal connector of the tubing line; and
   a pressure sensor comprising a cuff, a force transmitting member, and a transducer, the cuff including an inner surface and an outer surface, the inner surface configured to fit around the tubing line, the transducer being embedded in the cuff, between the inner surface and the outer surface, and the force transmitting member being coupled to the transducer and exposed at the inner surface of the cuff; and wherein the cuff is sized so that an outer surface of the tubing line contacts the force transmitting member of the pressure sensor, when the cuff is properly fitted around the tubing line, wherein the pressure sensor further comprises a microprocessor coupled to the transducer thereof for receipt of transducer signals, the microprocessor being programmed to characterize a transducer signal in response to the force transmitting member, after the cuff is fitted around the tubing line, and while the lumen of the tubing line is open to atmospheric pressure, to detect whether or not the cuff is properly fitted around the tubing line, and wherein the microprocessor is adapted to send a signal to an injector of the injection system, after detecting that the cuff is properly fitted around the tubing line, the signal unlocking the injector for operation.

5. The assembly of claim 1, wherein the cuff of the pressure sensor further includes a slit, extending from the outer surface thereof to the inner surface thereof, and a hinge opposite the slit, such that the cuff may be opened for radial insertion and withdrawal of the tubing line into and out from the cuff; and wherein the slit includes a locking feature for securing the cuff around the tubing line.

6. The assembly of claim 4, wherein:
the tubing line includes a first length and a second length, the first length extending distally from the proximal connector and having a wall of a first compliance, and the second length extending distally from the first length and having a wall of a second compliance, the second compliance being greater than the first compliance.

7. The assembly of claim 6, wherein the second length of the tubing line is located in close proximity to the distal connector.

8. The assembly of claim 6, wherein the second length of tubing line has a larger outer diameter than the first length of the tubing.

9. The assembly of claim 4, wherein the cuff of the pressure sensor further includes a slit, extending from the outer surface thereof to the inner surface thereof, and a hinge opposite the slit, such that the cuff may be opened for radial insertion and withdrawal of the tubing line into and out from the cuff; and wherein the slit includes a locking feature for securing the cuff around the tubing line.

10. A pressure sensor for a medical injection system, the sensor comprising:
a cuff including an outer surface and an inner surface, the inner surface being configured to fit around a tubing line of the system, the tubing line defining a lumen;
a transducer embedded in the cuff between the inner surface of the cuff and the outer surface of the cuff; and
a force transmitting member coupled to the transducer and exposed at the inner surface of the cuff, such that an outer surface of the tubing line, when properly fitted within the cuff, contacts the force transmitting member;
further comprising a microprocessor coupled to the transducer thereof for receipt of transducer signals, the microprocessor being programmed to characterize a transducer signal in response to the force transmitting member, after the tubing line is fitted within the cuff, and while the lumen of the tubing line is open to atmospheric pressure, to detect whether or not the tubing line is properly fitted within the cuff, and, or to determine a characteristic of the tubing line, wherein the microprocessor is adapted to send a signal to an injector of the injection system, after detecting that the cuff is properly fitted around the tubing line, the signal unlocking the injector for operation.

11. The sensor of claim 10, wherein the inner surface of the cuff is further configured to enclose a length of the properly fitted tubing line, such that an entire perimeter of the inner surface of the cuff is in close proximity to the enclosed length of the tubing line, when pressures within the tubing line are at, or above, approximately atmospheric pressure; and the inner surface of the cuff supports the enclosed length of the tubing against plastic deformation when pressures within the tubing line are significantly greater than atmospheric pressure.

12. The sensor of claim 10, wherein the cuff further includes a slit, extending from the outer surface thereof to the inner surface thereof, and a hinge opposite the slit, such that the cuff may be opened for radial insertion and withdrawal of the tubing line into and out from the cuff; and wherein the slit includes a locking feature for securing the cuff around the inserted the tubing line.

* * * * *